(12) United States Patent
Knoepfle et al.

(10) Patent No.: US 10,292,742 B2
(45) Date of Patent: May 21, 2019

(54) IMPLANT FOR BONE FIXATION

(71) Applicant: Stryker European Holdings I, LLC, Kalamazoo, MI (US)

(72) Inventors: Christian Knoepfle, Donaueschingen (DE); Karl Greiner, Muehlheim (DE); Manfred Schmuck, Muehlheim (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 418 days.

(21) Appl. No.: 14/991,181

(22) Filed: Jan. 8, 2016

(65) Prior Publication Data

US 2016/0199111 A1 Jul. 14, 2016

(30) Foreign Application Priority Data

Jan. 9, 2015 (EP) .................................. 15000033

(51) Int. Cl.
*A61B 17/82* (2006.01)
*A61B 17/00* (2006.01)
(Continued)

(52) U.S. Cl.
CPC .......... *A61B 17/82* (2013.01); *A61B 17/8076* (2013.01); *A61B 17/823* (2013.01);
(Continued)

(58) Field of Classification Search
CPC . A61B 17/80; A61B 17/8052; A61B 17/8076; A61B 17/82
See application file for complete search history.

(56) References Cited

U.S. PATENT DOCUMENTS 4,535,764 A * 8/1985 Ebert ..................... A61B 17/06 24/23 EE
5,417,698 A 5/1995 Green et al.
(Continued)

FOREIGN PATENT DOCUMENTS

CN 202235628 U 5/2012
EP 0597259 A2 5/1994
(Continued)

OTHER PUBLICATIONS

Extended European Search Report for Application No. 15000033.9 dated Jun. 24, 2015.
(Continued)

*Primary Examiner* — Christopher Beccia
(74) *Attorney, Agent, or Firm* — Lerner, David, Littenberg, Krumholz & Mentlik, LLP

(57) ABSTRACT

An implant for bone fixation is presented. The implant comprises an elongated member configured to be wound around bone parts that are to be fixed. Further, an engagement feature is provided that is coupled to the elongated member and configured to engage a portion of the elongated member so as to secure the implant in a loop around the bone parts. A fastening member is arranged between and coupled to the elongated member and the engagement member. The fastening member comprises at least one opening for receiving a bone fastener. In one variant, at least one visual indicator indicating a region of the fastening member to be severed in order to detach the implant is provided. In another variant, at least one of the engagement member and the elongated member are coupled to the fastening member by injection molding.

17 Claims, 8 Drawing Sheets

(51) Int. Cl.
*A61B 17/80* (2006.01)
*A61B 17/86* (2006.01)
*A61B 90/00* (2016.01)

(52) U.S. Cl.
CPC ....... *A61B 17/8052* (2013.01); *A61B 17/8085* (2013.01); *A61B 17/86* (2013.01); *A61B 2017/00407* (2013.01); *A61B 2017/00526* (2013.01); *A61B 2017/00955* (2013.01); *A61B 2090/037* (2016.02)

(56) References Cited

U.S. PATENT DOCUMENTS

| | | | |
|---|---|---|---|
| 5,941,881 | A | 8/1999 | Barnes |
| 6,872,210 | B2 | 3/2005 | Hearn |
| 8,460,295 | B2 | 6/2013 | McClellan et al. |
| 8,486,114 | B2 | 7/2013 | Gillard et al. |
| 2002/0128654 | A1* | 9/2002 | Steger ............... A61B 17/8047 606/291 |
| 2003/0212399 | A1 | 11/2003 | Dinh et al. |
| 2005/0070928 | A1 | 3/2005 | Heino et al. |
| 2005/0267475 | A1 | 12/2005 | Miller |
| 2006/0116683 | A1 | 6/2006 | Barrall et al. |
| 2006/0259141 | A1 | 11/2006 | Roman et al. |
| 2006/0276794 | A1 | 12/2006 | Stern |
| 2008/0154312 | A1 | 6/2008 | Colleran et al. |
| 2010/0094294 | A1 | 4/2010 | Gillard et al. |
| 2011/0015681 | A1* | 1/2011 | Elsbury ............... A61B 17/7059 606/286 |
| 2011/0295257 | A1 | 12/2011 | McClellan et al. |
| 2014/0100573 | A1* | 4/2014 | Llas Vargas ....... A61B 17/8869 606/74 |
| 2014/0142638 | A1* | 5/2014 | Goodwin ............. A61B 17/842 606/281 |
| 2015/0045794 | A1* | 2/2015 | Garcia ............... A61B 17/8076 606/74 |

FOREIGN PATENT DOCUMENTS

| | | |
|---|---|---|
| EP | 0608592 A1 | 8/1994 |
| EP | 1654994 A1 | 5/2006 |
| WO | 02/067795 A1 | 9/2002 |
| WO | 2006135935 A1 | 12/2006 |
| WO | 2010042946 A1 | 4/2010 |
| WO | 2014144479 A1 | 9/2014 |

OTHER PUBLICATIONS

European Search Report for EP 13003896.1 dated Jul. 17, 2014.
International Search Report and Written Opinion for Application No. PCT/EP2013/066408 dated Oct. 22, 2013.
International Preliminary Report on Patentability Chapter II, for Application No. PCT/EP2013/066408 dated Sep. 25, 2015.

* cited by examiner

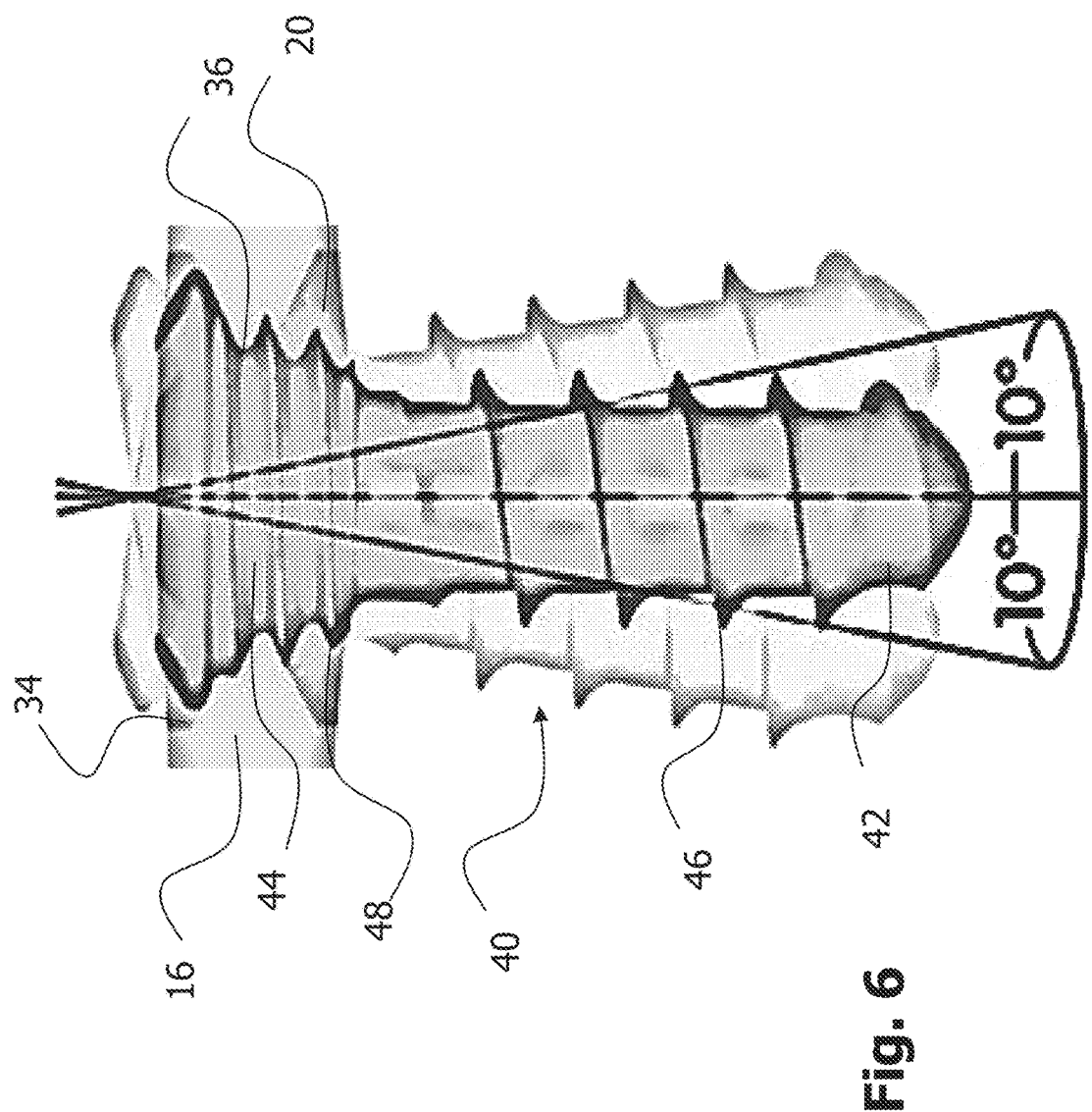

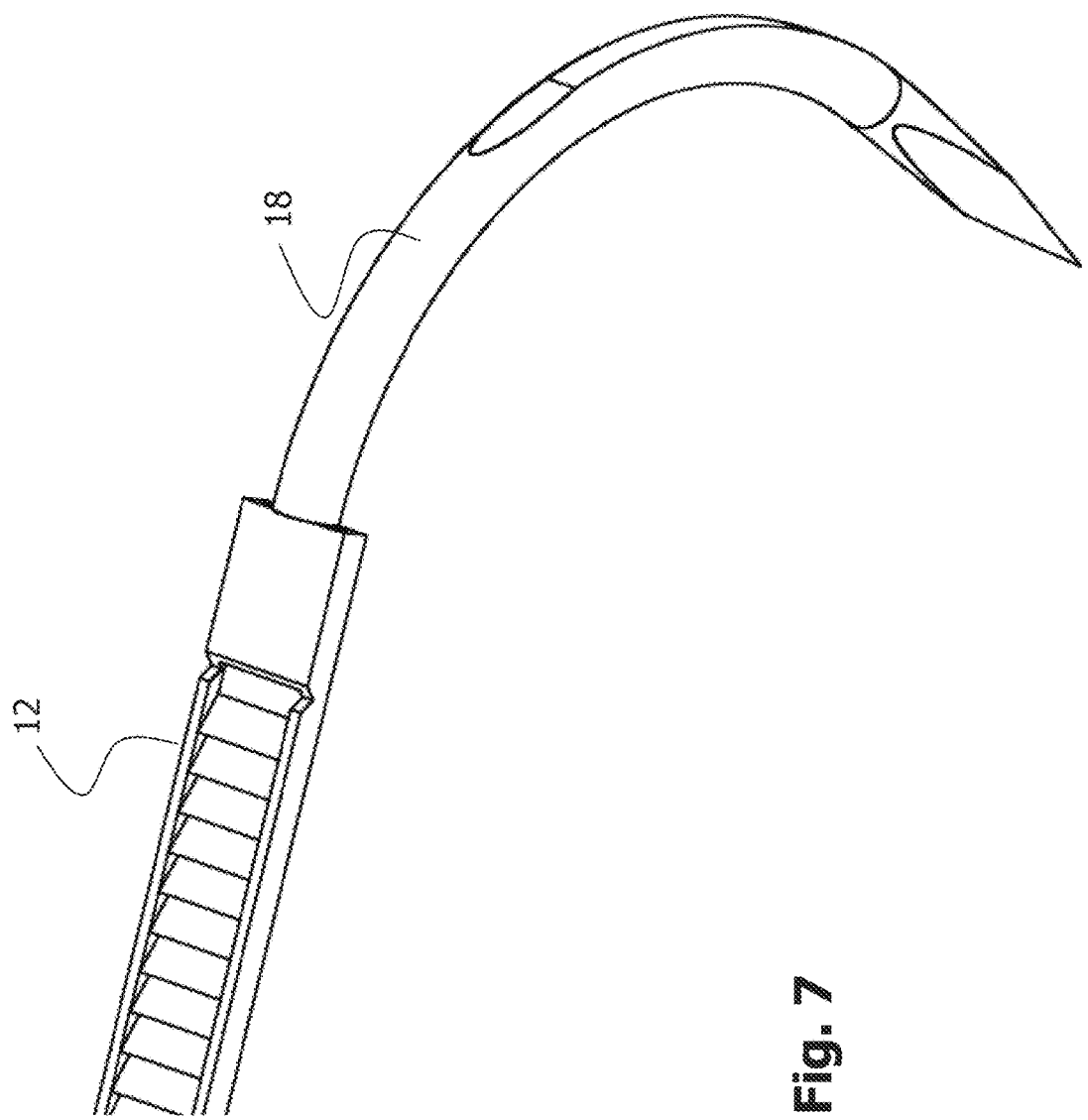

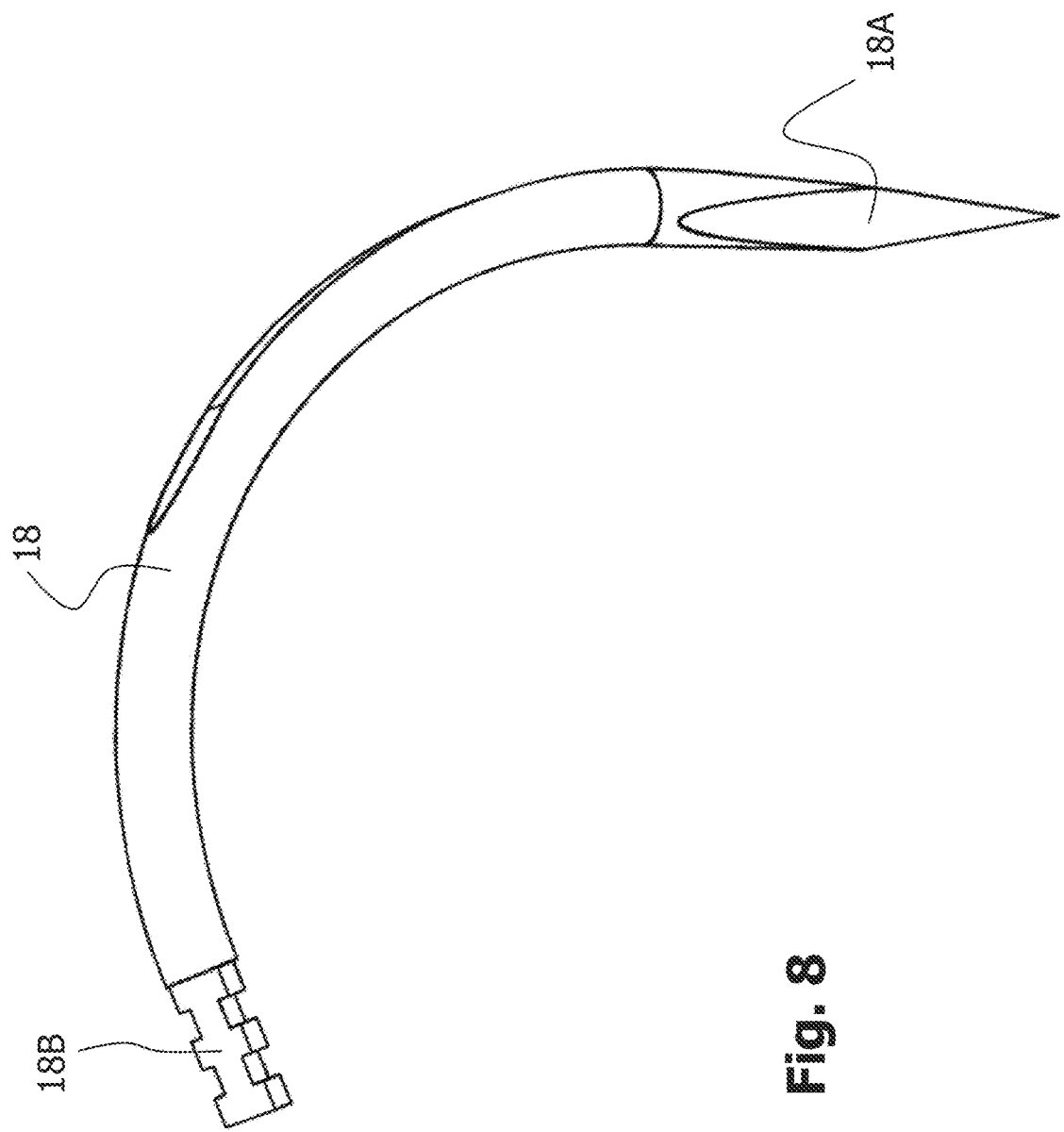

IMPLANT FOR BONE FIXATION

CROSS-REFERENCE TO RELATED APPLICATION

The present application claims priority from European Patent Application No. 15 000 033.9 filed Jan. 9, 2015 the disclosure of which is hereby incorporated herein by reference.

TECHNICAL FIELD

The present disclosure generally relates to bone fixation. Specifically, the disclosure relates to an implant for fixing bone parts, to systems comprising the implant, and to methods of manufacturing the implant.

BACKGROUND OF THE INVENTION

Various surgical procedures require the surgeon to access the thoracic region of a patient. A known approach to access the thoracic region is to cut the sternum in two parts and separate these two parts from each other for gaining access to the thoracic region. After completion of the surgical procedure, the separated parts of the sternum are brought back to their initial positions and fixed, for example, with a bone plate attached to the sternum parts or a wire tensioned around the circumference of the sternum.

U.S. Pat. No. 5,417,698 discloses a closure element to be looped around a human sternum. The closure element comprises a strap which is inserted through and retained by a tightening plate.

U.S. Pat. No. 8,460,295 discloses a sternum repair device including a central body and a plurality of bands extending from the central body. The bands are wrapped around the sternum to keep the sternum parts together. The central body includes a view window which is used by a surgeon to line up the device during installation on the sternum.

U.S. Pat. No. 8,486,114 discloses a cerclage system including a cable that encircles the sternum parts and a bone plate having channels to receive segments of the cable. The bone plate further includes a pair of locking studs to lock the cable within the channels to the bone plate.

EP 0 608 592 B1 discloses an assembly for banding a sternum. The assembly comprises an elongated flexible band, a needle at one end of the band and a buckle proximate the other end of the band. A main section of the band includes a plurality of spaced apart slots which can engage at a locking mechanism.

After the thoracic procedure such as, for example, a bypass operation has been carried out on a patient and the sternum parts have been fixed using a suitable fixation assembly, the patient is normally kept under surveillance. If it is detected that the surgical procedure has failed or that complications occur, it may be desirable for the surgeon to again open the fixation system for accessing the thoracic region. The time required for this opening procedure may be critical for the patient's health and even life.

In other situations, a cable or wire tensioned around the sternum parts (so-called "primary closure") might become loose or break due to the load applied to the thoracic region of the patient. In such cases, the sternum part fixation may need to be stabilized by, for example, a bone plate (so-called "secondary closure").

Similar or related problems occur in connection with other surgical procedure in which two or more bone parts need to be fixed.

There is a need for an implant for bone fixation that can be attached or separated fast, easily and at low risk for the patient. Furthermore, there is a need for such an implant which provides a high implant-bone-construct-stability. Moreover, there is generally a need for an implant for bone fixation that exhibits good surgical results.

SUMMARY OF THE INVENTION

According to a first aspect of the present invention an implant for bone fixation is provided. The implant comprises an elongated member, an engagement member, a fastening member, and at least one visual indicator. The elongated member is configured to be wound around bone parts that are to be fixed and the engagement member is coupled to the elongated member and configured to engage a portion of the elongated member so as to secure the implant in a loop around the bone parts. The fastening member is arranged between and coupled to the elongated member and the engagement member, the fastening member comprising at least one opening for receiving a bone fastener. The at least one visual indicator indicates a region of the fastening member to be severed in order to detach the implant.

In some implementations, at least the elongated member and the fastening member may be made of different materials. As an example, the elongated member may be made from a material that exhibits a certain flexibility so that the elongated member can be wound around the bone parts. On the other hand, the fastening member may be made from a rigid material that will not, or not easily, deform upon an engagement with the bone fastener. As such, the rigidity of the fastening member material may generally be higher than the rigidity of the engagement member material.

In a first realization, the region of the fastening member indicated by the visual indicator may be a region of reduced mechanical strength of the fastening member. As such, the mechanical strength of the fastening member may be lower in the region indicated by the visual indicator than in other regions of the fastening member. The mechanical strength may be defined in relation to a force required to sever (cut, saw, etc.) the fastening member. In another realization, that may be combined with the first realization, the region of the fastening member indicated by the visual indicator may be a region that is to be severed from a surgical viewpoint (e.g., so as to separate the bone parts).

The fastening member may be coupled to at least one of the elongated member and the engagement member by injection molding. In one variant, the fastening member comprises a first end and a second end opposite to the first end. The elongated member may be injection molded to the first end of the fastening member. Additionally, or as an alternative, the engagement member may be injection molded to the second end of the fastening member. As an example, the elongated member may be injection molded to the first end of the fastening member in a first injection molding process and the engagement member may be injection molded to the second end of the fastening member in a second injection molding process separate from the first injection molding process. The first and second injection molding processes may be performed at separate points in time (e.g., one after the other) or substantially at the same point in time (e.g., simultaneously).

If injection molding is used for manufacturing the implant, the visual indicator may be defined by a portion of the fastening member that remains exposed from injection molding. As an example, the exposed region may be located between the first end of the fastening member associated with the first injection molding process and the second end of the fastening member associated with the second injection molding process. The exposed region may have a width of 1 to 10 mm.

Regardless of the manufacturing process, the visual indicator may also be realized in any other manner. As an example, the visual indicator may be printed on the implant. Additionally, or in the alternative, the visual indicator may be realized as a three-dimensional structure, for example so as to comprise a notch or a groove. As will be appreciated, such a three-dimensional structure could also facilitate severing of the fastening member.

The visual indicator may in one variant extend in a direction substantially perpendicular to an extension of the elongated member. For example, the visual indicator may indicate a direction in which the fastening member is to be severed. In another variant, the visual indicator may have no preferred extension (e.g., it may take the form of a point, circle, or similar non-directed feature).

The fastening member may comprise a plurality of openings. In this regard, the fastening member may comprise at least a first opening and a second opening that are substantially aligned with an extension of the elongated member. The visual indicator may be located between the first opening and the second opening. In variants in which the fastening member comprises more than two openings, still a single visual indicator may be provided (e.g., separating the plurality of openings in two sets of two or more openings each).

In a fastening member with several openings, the first opening may be configured to be located proximate to a first bone portion and the second opening may configured to be located proximate to a second bone portion to be fixed. There may be further openings located proximate to the first and second bone portions, respectively (e.g., to insert two or more bone fasteners in each bone portion).

In a second aspect of the present invention, a further implant for bone fixation is provided. The implant comprises an elongated member configured to be wound around bone parts that are to be fixed, an engagement member coupled to the elongated member and configured to engage a portion of the elongated member so as to secure the implant in a loop around the bone parts, and a fastening member arranged between and coupled to the elongated member and the engagement member. The fastening member comprises at least one opening for receiving a bone fastener and is coupled to at least one of the elongated member and the engagement member by injection molding.

The implant of the second aspect may comprise a visual indicator as generally discussed herein. In other variants, no such visual indicator may be provided.

In all the implant aspects presented herein, the elongated member may comprise a plurality of engagement features provided along an extension of the elongated member. In such a case, the engagement member may be configured to be brought into selective engagement with one of the engagement features. In one variant, the engagement features and the engagement member realize a zip tie-type engagement mechanism.

In all the implant aspects, a hook member may be coupled to the elongated member at an end thereof opposite to the engagement member. The hook member may be coupled to the elongated member by injection molding or may form an integral part of the elongated member.

In all the implant aspects, the at least one opening of the fastening member may comprise a locking feature configured to lock the bone fastener to the fastening member.

Further, the locking feature may be configured to engage the bone fastener at a selected angular orientation. The locking feature may take the form of a circumferential lip (e.g., of increased material thickness) or of a thread. The at least one opening of the fastening member may comprise a threaded portion on a bone facing side of the fastening member and an unthreaded portion on a side opposite to the bone facing side.

A portion of the fastening member adjacent to the at least one opening may have a conical, convex or spherical taper which substantially tapers inwardly in a direction toward a bone facing surface of the fastening member. Thus, the fastening member can be configured to exert a compression force when a bone fastener is screwed or inserted through the opening into a bone part.

In one implementation, the at least one opening of the fastening member may be adjacent to an inclined surface onto which a bone fastener is able to slide in a fastening or compression position. The inclined surface may permit a bone fastener to slide laterally or longitudinally with respect to the opening or the fastening member. Further, at least one opening of the fastening member may define a predetermined direction for a bone fastener. The inclined surface may have a predetermined angle with respect to an extension plane of the attachment member. The predetermined angle can be between about 20 and 70 degrees, for example about 40 to 50 degrees (e.g., about 45 degrees).

The at least one opening of the fastening member may generally be a circular or elongated hole. The elongated hole may be an oblong hole. Further, the elongated hole may extend substantially parallel with respect to a longitudinal direction of the fastening member or of the flexible elongated member. Alternatively, the elongated hole may extend substantially perpendicular to a longitudinal direction of the fastening member or of the elongated member.

The implant may have a larger width in a region of the one or more openings compared to a general width of the elongated member. The thickness of the fixation assembly may be larger in a region of the one or more openings compared to a general thickness of the elongated member.

In all the implant aspects, the fastening member may be made from a metallic material (e.g., stainless steel, titanium or a titanium alloy). In addition, or as an alternative, at least one of the elongated member and the engagement member may be made from a polymeric material (e.g., polyetheretherketone, PEEK). In certain variants, the engagement member and the fastening member may at least partially be realized as a one-piece structure. As such, the engagement member may at least partially be made from the same material than the fastening member.

Also provided is a an implant system comprising the implant presented herein and at least one bone fastener configured to be inserted through the at least one opening of the fastening member into bone.

As said, the at least one opening may comprise a first locking feature configured to lock the bone fastener to the fastening member. In such a case the bone fastener may comprise a second locking feature configured to engage the first locking feature. As an example, the first locking feature may take the form of a circumferential lip or thread. The second locking feature may take the form of a thread. This thread may be provided in a head region of the bone fastener or immediately below the head region. The second locking feature may be different from a bone engaging thread of the bone fastener.

Still further, a method of manufacturing an implant is provided, wherein the implant has an elongated member configured to be wound around bone parts that are to be fixed, an engagement member coupled to the elongated member and configured to engage a portion of the elongated member so as to secure the implant in a loop around the bone parts, and a fastening member arranged between and coupled to the elongated member and the engagement member, the fastening member comprising at least one opening for receiving a bone fastener. The method comprises coupling the fastening member to at least one of the elongated member and the engagement member by injection molding.

The method aspect may comprise one or more further steps or substeps to manufacture the implant presented herein.

BRIEF DESCRIPTION OF THE DRAWINGS

The above and other features, aspects and advantages of the present disclosure will now be explained with reference to the following description of exemplary embodiments and the accompanying drawings, wherein:

FIG. 6 is a schematic cross-sectional view illustrating an angular orientation of a bone fastener relative to a fastening member in accordance with a further embodiment;

FIG. 7 is an enlarged perspective view of another portion of the implant of FIG. 1; and FIG. 8 is a perspective view of a hook member of the implant of FIG. 1.

DETAILED DESCRIPTION

Figure 1:
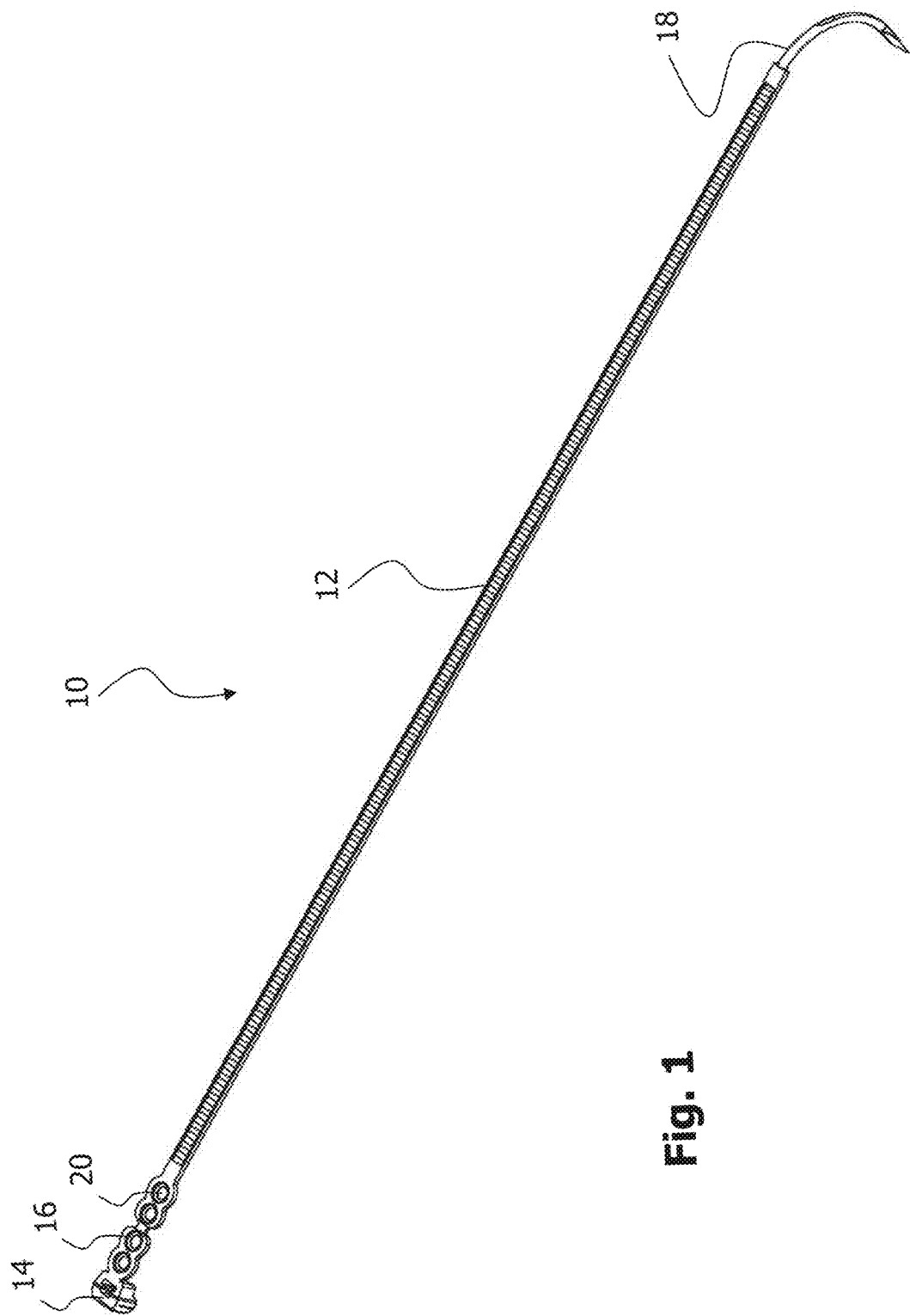
FIG. 1 is a perspective view of an embodiment of an implant for bone fixation.

In the following description, exemplary embodiments of a bone fixation implant and an implant system comprising the implant and a bone fastener will be explained with reference to the drawings. The same reference numerals will be used to denote the same or similar structural features.

FIG. 1 shows a perspective view of an embodiment of a bone fixation implant 10. In the embodiment shown in FIG. 1, the implant 10 is configured and dimensioned for fixing bone parts of a sternum. It will be appreciated that the present disclosure is not limited to this surgical indication. Rather, the present disclosure can also be applied in connection with fixing bone parts in other regions of the human anatomy, possibly with suitably adapted configurations and dimensions.

The implant 10 shown in FIG. 1 comprises an elongated member 12, an engagement member 14 coupled to the elongated member 12, and a fastening member 16 arranged between and coupled to the elongated member 12 and the engagement member 14.

The elongated member 12 is configured to be wound around the sternum parts that are to be fixed. As such, the elongated member 12 is made from a generally flexible material and has a suitable length of approximately 10 to 35 cm. The engagement member 14 is configured to engage a portion of the elongated member 12 so as to secure the implant 10 in a loop around the sternum parts. Details of how the engagement member 14 engages the elongated member 12 will be described in more detail below.

As also shown in FIG. 1, the implant 10 further comprises a hook member 18 coupled to the elongated member 12 at an end thereof opposite to the engagement member 14. The hook member 18 is configured to facilitate threading of the elongated member 12 around the sternum parts that are to be fixed. It will be appreciated that depending on the surgical indication, the hook member 18 could also be omitted or substituted by another member (e.g., a linear needle) to support a proper placement of the elongated member 12 by a surgeon.

In the following, the configuration of the implant portion comprising the engagement member 14 and the fastening member 16 will be described in more detail with reference to FIGS. 2 and 3. As illustrated therein, the fastening member 16 comprises a plurality of openings 20. Each opening 20 is configured to receive a bone fastener such as a bone screw or a bone pin. The openings 20 are substantially aligned with an extension of the elongated member 12. In the exemplary case of openings 20 having a circular shape, the centers of the openings 20 lie on an axis that coincides with an axis of the elongated member 12 in a non-wound (i.e., planar) state.

The fastening member 16 of the present embodiment comprises four openings 20. It will be appreciated that more or less openings 20 could be provided in other embodiments depending on the surgical needs.

Figure 2:
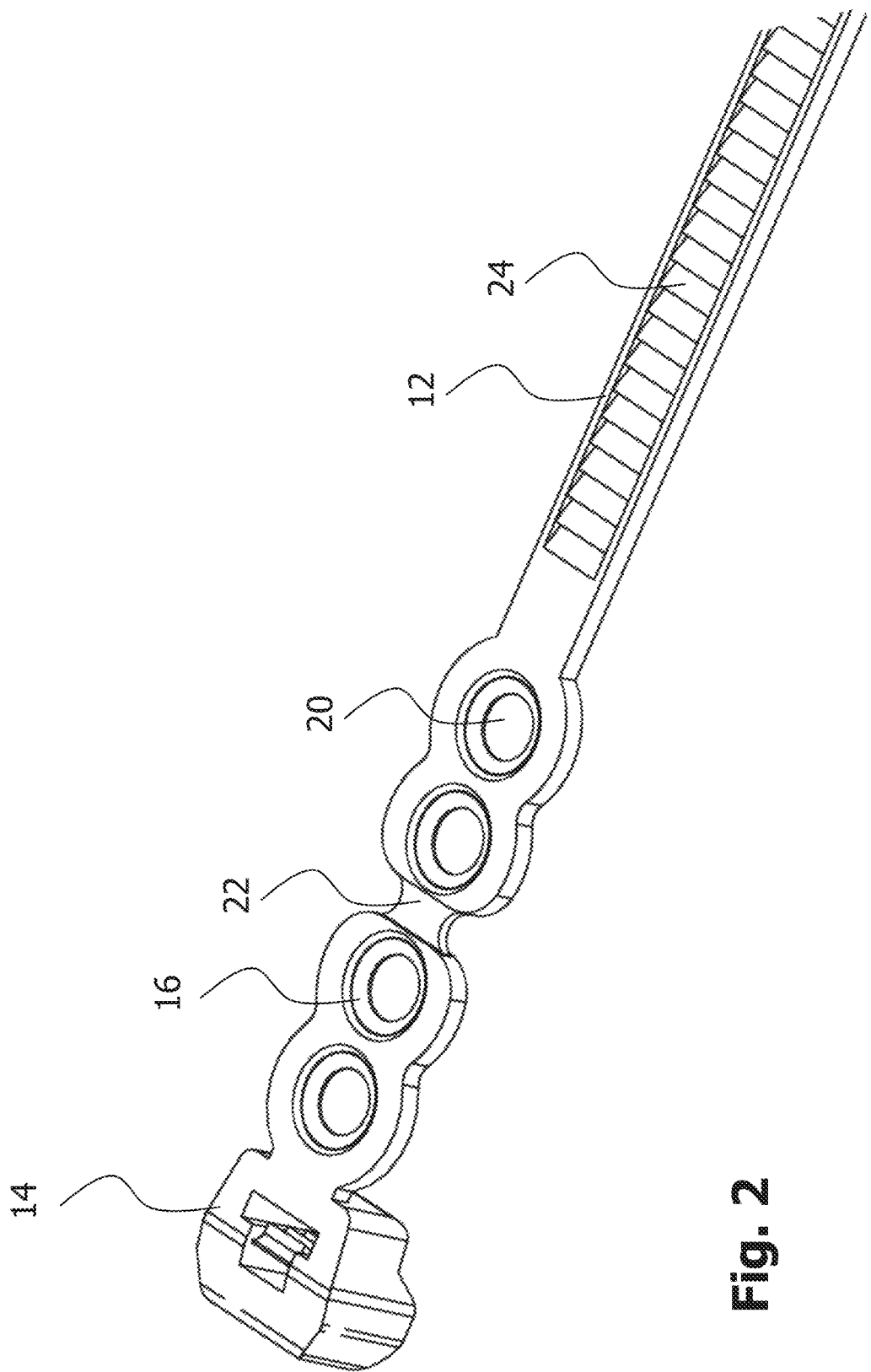
FIG. 2 is an enlarged perspective view of a portion of the implant of FIG. 1.
Figure 3:
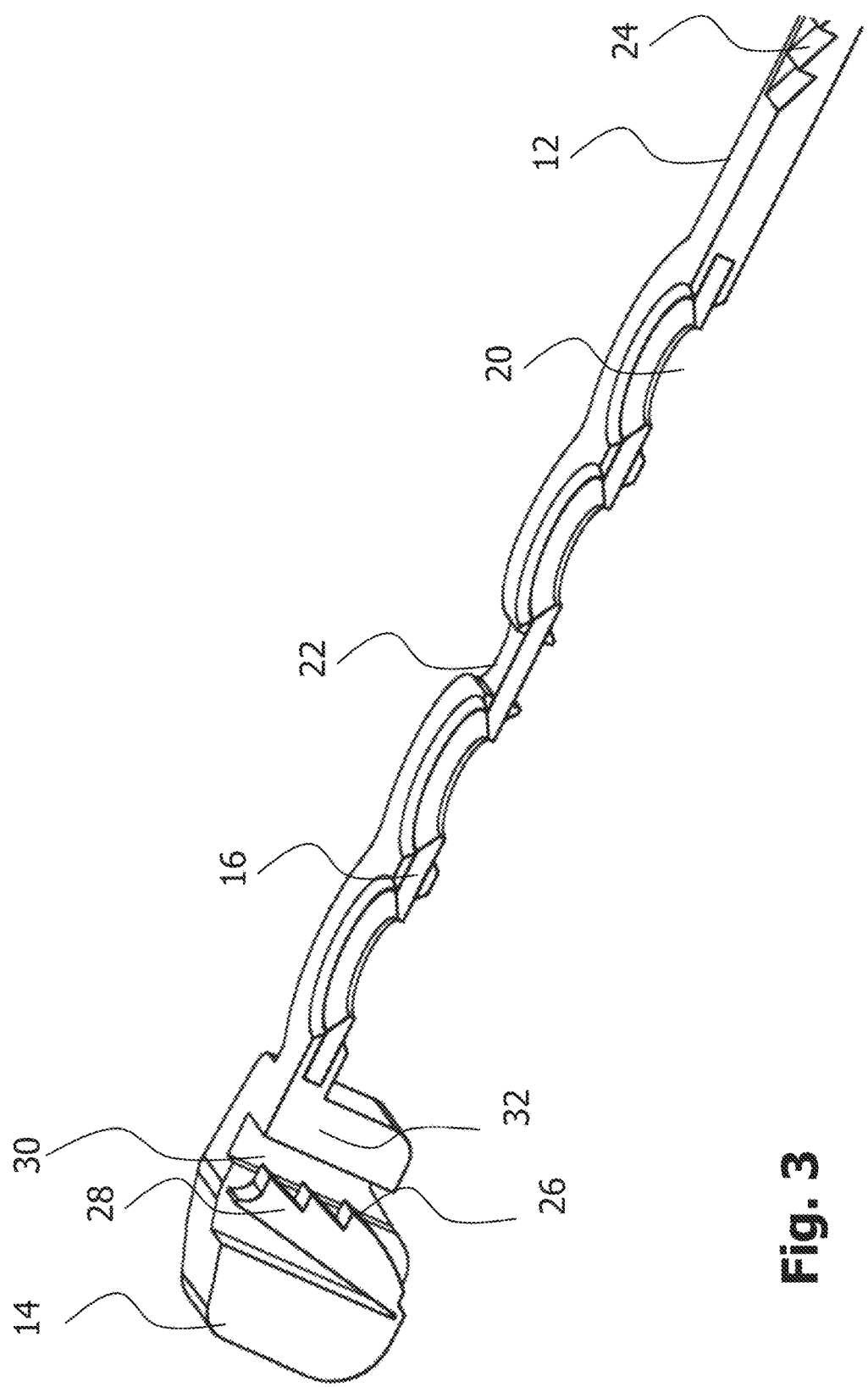
FIG. 3 is a perspective cross-sectional view of the implant portion shown in FIG. 2.

As illustrated in FIGS. 2 and 3, the four openings 20 are divided by a visual indicator 22 into two sets of two openings 20 each. The visual indicator 22 indicates a region of the fastening member 16 to be severed in order to detach the implant 10 after implantation. In the present embodiment, the visual indicator 22 has a generally rectangular shape with a larger extension that extends in a direction substantially perpendicular to the extension of the elongated member 12. The visual indicator 22 thus indicates the direction in which the fastening member 16 is to be severed.

The visual indicator 22 in the present embodiment marks a region of reduced mechanical strength of the fastening member 16 (explained in more detail below with reference to FIG. 4). As such, the visual indicator 22 indicates the region of the fastening member 16 that is easiest to sever by a surgical cutter in order to detach the implant 10.

In the context of fixing two sternum parts, the visual indicator 22 of the implant 10 after implantation will generally lie on a line along which the two sternum parts have been joined. That joining line will generally extend perpendicular to the extension of the fastening member 16. For this reason the visual indicator 22 separates a first set of two openings 20 that will be located proximate to one sternum portion from another set of two openings 16 that will be located proximate to the other sternum portion. Severing the fastening member in the region of the visual indicator 22 will therefore permit to separate the two sternum parts (e.g., in the case of medical complications) even when the bone fasteners attached via the openings 20 to the sternum parts remain in place.

It will be evident that severing the fastening member 16 in the region of the visual indicator 22 in order to detach the implant 10 provides a much quicker access to the thoracic region than detaching the implant 10 by removing multiple bone fasteners inserted to the openings 20 into the sternum parts. It should be noted that after severing the fastening member 16 it may still be required to also sever the elongated member 12 or another portion of the implant 10 to fully separate the sternum parts. In any case, the visual indicator 22 guides the surgeon towards the optimal fastening member region to be severed in order to quickly detach the implant 10.

The visual indicator 22 may generally be provided in many different ways, for example by printing it on the implant 10 (e.g., directly on the fastening member 10), by stamping a line or any other three-dimensional pattern in the implant 10 (e.g., directly in the fastening member 16), or in other ways. In the present embodiment, the visual indicator 22 is realized during the manufacturing process of the implant 10 by exposing a portion of the fastening member 16 during an injection molding process.

Specifically, as illustrated in FIG. 3, the fastening member 16 is coupled to the elongated member 12 and the engagement member 14 by injection molding. In this regard, the elongated member 12 is injection molded to a first end of the fastening member 16, while the engagement member 14 is injection molded to an opposite end of the fastening member 16. The visual indicator 22 is thus defined by a central portion of the fastening member 16 that remains exposed from injection molding.

In certain variants, the elongated member 12 is injection molded to the fastening member 16 in a first injection molding process and the engagement member 14 is injection molded to the fastening member 16 in a second injection molding process separate from the first injection molding process. The two injection molding processes may be performed essentially at the same point in time or at spaced apart points in time. It will further be appreciated that in certain embodiments the visual indicator 22 may be omitted. In such a case, or in other cases, the fastening member 16 may be injection molded to the elongated member 12 and to the engagement member 14 in a single injection molding process.

As will be appreciated, the fastening function of the fastening member 16 can best be fulfilled in case the fastening member 26 is made from a rigid material, such as metal (e.g., stainless steel, titanium, or a titanium alloy), especially if compression forces are to be applied via the bone fasteners inserted through the openings 20. On the other hand, the elongated member 12 will be manufactured from an at least partially flexible material since it needs to be wound around the bone parts that are to be fixed. As such, the elongated member can be made from a polymeric material such as PEEK.

The engagement member 14 may be made from the same material as the elongated member 12 or from a different material. As an example, the engagement member 14 may also be made from PEEK. In another variant, the engagement member 14 may at least partially be made from the same material as the fastening member 16. As an example, the engagement member 14 and the fastening member 16 may at least partially be realized as a one-piece structure.

As will be appreciated, using a polymeric material for the elongated member 12 and the engagement member 14 facilitates injection molding of those two members 12, 14 to the fastening member 16. However, the present disclosure in relation to the visual indicator 22 is not limited to manufacturing the implant 10 using one or more injection molding processes. Moreover, the visual indicator 22 could also be realized in connection with an implant 10 that is realized as a one-piece structure (e.g., from a polymeric material and, optionally, in a single injection molding process).

FIGS. 2 and 3 also illustrate the engagement mechanism that allows the engagement member 14 to engage a portion of the elongated member 12 so as to secure the implant 10 in a loop around the sternum parts. In more detail, the elongated member 12 comprises a plurality of engagement features 24 that are provided along essentially the entire length of the elongated member 12 (see FIG. 1). As can best be seen in FIG. 3, each individual engagement feature 24 has a sawtooth-like cross-section with a first surface that extends generally perpendicular to a plane defined by the elongated member 12 in an un-wound state, and a second surface at an angle to that plane.

The engagement member 14 comprises complementary engagement features 26 with a sawtooth-like profile. As shown in FIG. 3, those complementary engagement features 26 are provided on a deflectable pawl 28. The pawl 28 is located within an opening 30 that extends through a head portion 32 of the engagement member 14. The opening 30 has an axis that is substantially parallel to a center axis of each of the openings 20 in the fastening member 16.

The deflectable pawl 28 is attached to the head portion 14 at a bone facing side of the head portion 32 and configured to engage the engagement features 24 of the elongated member 12 in a zip tie-like manner upon threading the elongated member 12 through the opening 30 in the head portion 32 of the engagement member 14. The zip tie-like configuration of the engagement mechanism permits to generate a compression force when the implant 10 is looped around the sternum parts. This compression force presses the sternum parts against each other and facilitates bone healing.

It will be appreciated that in other embodiments other engagement mechanisms could be used. As an example, the elongated member 12 and the engagement member 14 could each also take the form of a band or wire that can be brought into engagement via knot or a dedicated coupling feature.

In the following, the configuration of the fastening member 16 will be described in more detail with reference to FIGS. 4 and 5. As shown therein, the fastening member 16 generally takes the form of an elongated bone plate with an undulating outer profile. Specifically, the undulations in the outer profile correspond to the location of the openings 20 in the fastening member 16. As can also be seen in FIG. 4, the central portion of the fastening member 16 (i.e., the region between a first set of two adjacent openings and a second set of two adjacent openings) has a reduced mechanical strength to facilitate severing of the fastening member 16. In more detail, the central portion of the fastening member 16 is the region of the fastening member 16 with the smallest width. As illustrated in FIGS. 2 and 3, that fastening member region with the smallest width corresponds to the location of the visual indicator 22.

Figure 4:
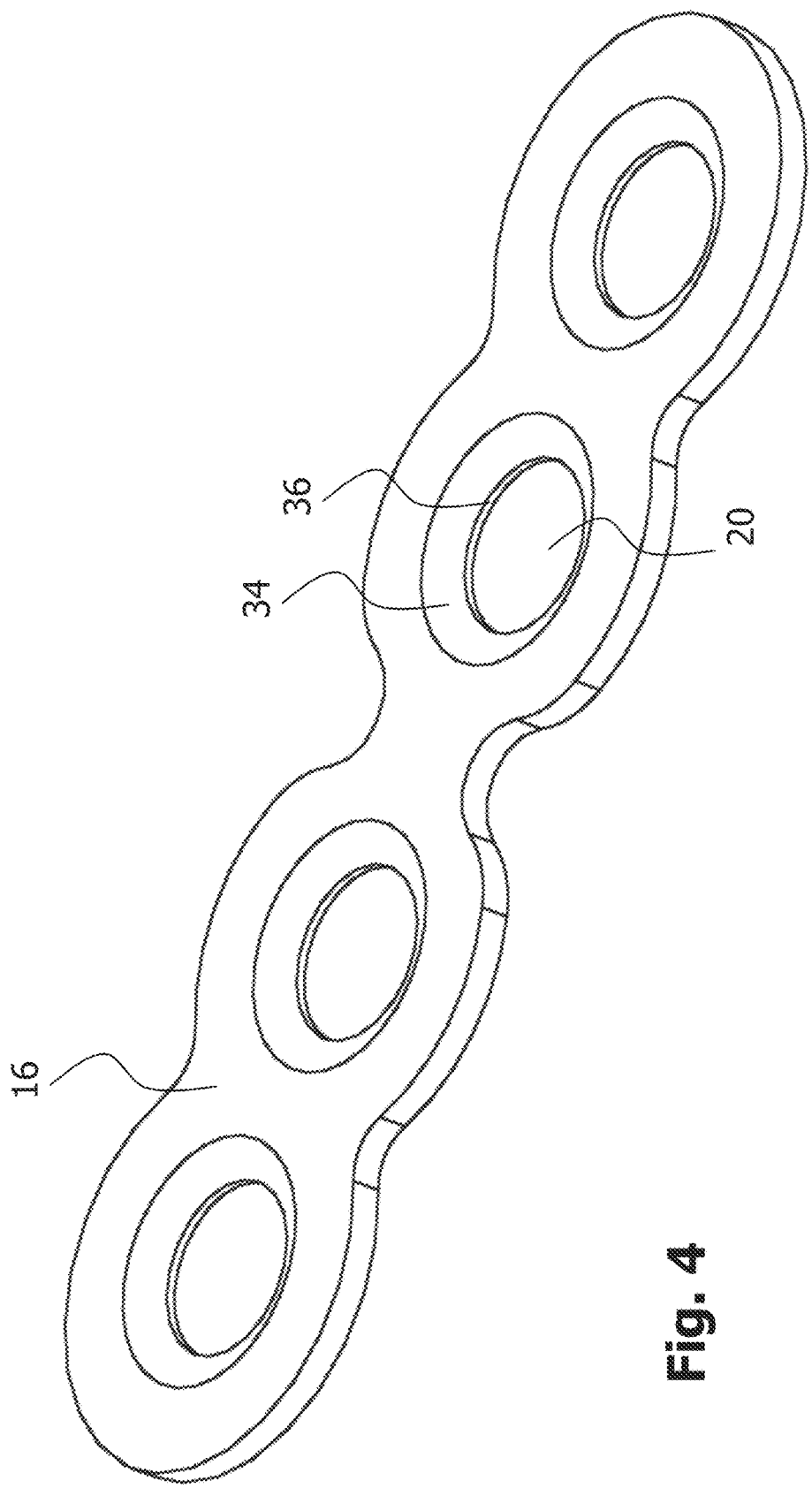
FIG. 4 is a perspective view of a fastening member for use in connection with the implant of FIG. 1.
Figure 5:
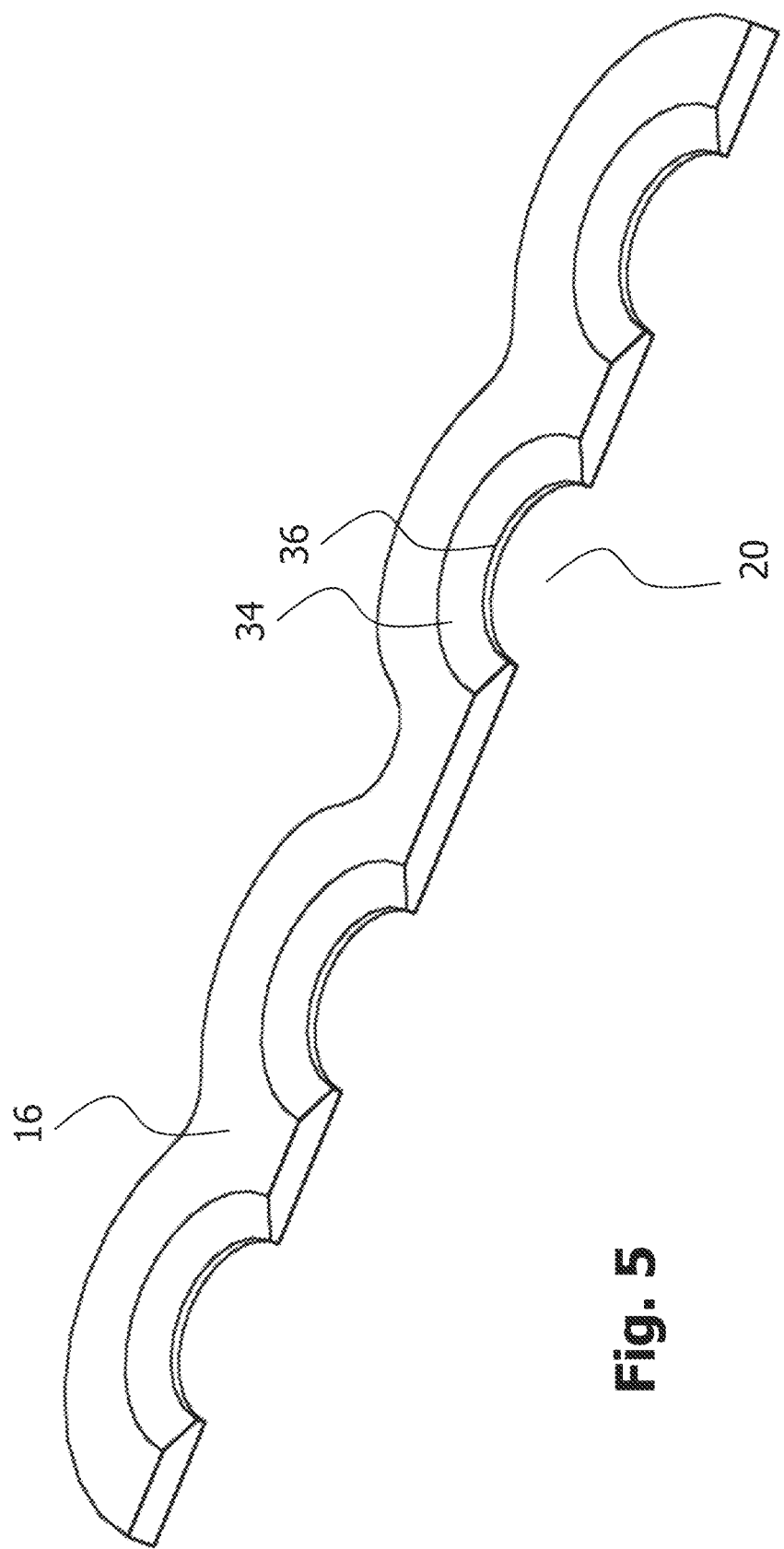
FIG. 5 is a perspective cross-sectional view of the fastening member shown in FIG. 4.

As also shown in FIGS. 4 and 5, the fastening member 16 comprises a conically tapering portion 34 towards each opening 20. In other embodiments, a spherical taper may be provided. The tapering portion 34 permits the generation of compression forces upon inserting a bone fastener through one of the openings 20. The compression forces result in the sternum parts being drawn towards the fastening member 16 so as to increase the implant-bone-construct-stability.

Further, each tapering portion 34 ends in a circumferential lip 36 of reduced material thickness around the respective hole 20. The lip 36 constitutes a locking feature configured to lock a bone fastener to the fastening member 16 as generally illustrated in FIG. 6 (for a different cross-sectional configuration of the fastening member 16).

FIG. 6 illustrates a bone screw 40 with a shaft 42 and a head 44. The shaft 42 of the bone screw 40 carries a bone thread 46 configured to engage bone. The head 44 of the bone screw 40 comprises a further thread 48 configured to engage the circumferential lip 36 at a selected angular orientation. As shown in FIG. 6, the selected angular orientation of the bone screw 40 may be within a range of 0° to 10° relative to the central axis of the opening 20. Upon screwing the bone screw 40 into bone, the thread 48 at the head portion 44 of the bone screw 40 will engage the circumferential lip 36 to lock the bone screw 40 at the selected angular orientation to the fastening member 14. As such, the thread 48 at the head 44 of the bone screw 40 constitutes a locking feature complementary to the circumferential lip 36 at the fastening member 16.

It will be appreciated that in other embodiments the circumferential lip 36 may be omitted or replaced by another locking feature, such as a thread. It will also be appreciated that in other embodiments the thread 48 provided at the head 44 of the bone screw 40 could also be omitted. In such a case the head 44 of the bone screw 40 could have a smooth and spherically or conically tapering configuration.

In the embodiment illustrated in FIG. 6, hole 20 tapers from a bone facing side of the fastening member 16 towards the lip 36 and also from the opposite side towards the circumferential lip 36. One or both of those tapers could be omitted.

Finally, FIGS. 7 and 8 illustrate the hook member 18 as well as the attachment of the hook member 18 to the elongated member 12. As shown in FIG. 8, the hook member 18 comprises a sharpened tip 18A at one end thereof as well as a structured region 18B at the opposite end. The structured region 18B facilitates injection molding of the elongated member 12 to the hook member 18, as generally illustrated in FIG. 7.

In the following, an exemplary method of using the implant 10 in connection with fixing two sternum parts will briefly be described. Similar methods may be applied in connection with other surgical indications for fixing bone parts in other regions of the human anatomy. In certain procedures, two sternum parts or portions may be separated by a bone cut. After these parts have been brought back together and preferably into their initial position with respect to one another, implant 10 is used for securing together these parts. U.S. Ser. No. 14/895,163 titled "Fixation Assembly with a Flexible Elongated Member for Fixing Parts of a Sternum," discloses in FIG. 10 thereof a fixation assembly attached to a sternum with bone parts having been brought back together and is hereby incorporated by reference herein in its entirety.

In a first step, the elongated member 12 is wound around the two sternum parts that are to be fixed. Winding the elongated member 12 around the sternum parts is facilitated by the hook member 18 with the sharpened tip 18A.

In a next step the hook member 18 and then the elongated member 12 are threaded through the opening 30 of the engagement member 14. In certain variants, the hook member 18 may be cut prior to that threading step, so that only the free end of the elongated member 12 (without the hook member 18) is threaded through the corresponding opening 30. Once the elongated member 12 enters the opening 30, the engagement features 24 on the elongated member 12 are engaged by the complementary engagement feature 26 on the pawl 29 in a zip tie-like manner (i.e., such that the elongated member 12 can only be tightened, but cannot become loose).

Then, the elongated member 12 is further drawn through the opening 30 so as to tighten the implant 10 around the two sternum parts. During that tightening process, the surgeon observes that the visual indicator 22 will substantially be placed on the joining line of the two sternum parts to enable a proper detachment. The tightening force is then increased further so as to compress the sternum parts together.

If only a primary closure is needed, the above steps may be repeated one or multiple times for one or more further implants 10. For primary closure, no further fixing of the implant 10 to the sternum parts using bone fasteners is needed.

On the other hand, in case of a need for secondary closure, one or two fixation members are inserted in each bone part through the respective openings 20. As has been explained above with reference to FIG. 6, each bone fasteners may be inserted at a selected angular orientation and may be locked to the implant 10 using the corresponding locking features 36, 48. The bone fasteners 40 may each have a self-drilling thread 46. Alternatively, pilot holes may be drilled through the openings 20 prior to insertion of the bone fasteners 40. In both cases, the thread 46 may be self-tapping.

If a surgeon requires quick access to the thoracic region after the implant 10 has been implanted using one or more bone fasteners 40, the surgeon uses a cutter to sever the fasting member 16 in the region of the visual indicator 22. In a further step, the surgeon cuts the elongated member 12 so the sternum parts can be separated from each other. The bone fasteners 40 may remain in place until after the thoracic region needs to be closed again via a primary or secondary closure process.

The features described in the above description and illustrated in the accompanying drawings can be modified, replaced or combined to result in different embodiments. It will thus be apparent that the present disclosure may be varied in many ways. Such variations are not to be regarded as a departure from the scope of the present disclosure, and they are intended to be included within the scope of the following claims.

The invention claimed is:

1. An implant for bone fixation, comprising:
   an elongated member defining a width between a first lateral side of the elongated member and a second lateral side of the elongated member, the elongated member being configured to be wound around bone portions that are to be fixed;
   an engagement member coupled to the elongated member and configured to engage a portion of the elongated member so as to secure the implant in a loop around the bone portions; and
   a fastening member arranged between and coupled to the elongated member and the engagement member, the fastening member comprising at least one opening for receiving a bone fastener and a region configured to be severed in order to open the loop of the implant, the fastening member being coupled to at least one of the elongated member and the engagement member by injection molding,
   wherein a portion of the region configured to be severed is located between a first axis collinear with the first lateral side and a second axis collinear with the second lateral side.

2. The implant of claim 1, wherein the region configured to be severed is a region of reduced mechanical strength of the fastening member.

3. The implant of claim 1, wherein the fastening member comprises a first end and a second end opposite to the first end, wherein the elongated member is injection molded to the first end of the fastening member and/or the engagement member is injection molded to the second end of the fastening member.

4. The implant of claim 3, wherein the elongated member is injection molded to the first end of the fastening member in a first injection molding process and wherein the engagement member is injection molded to the second end of the fastening member in a second injection molding process separate from the first injection molding process.

5. The implant of claim 1, wherein the region configured to be severed is defined by a portion of the fastening member that remains exposed from injection molding.

6. The implant of claim 1, wherein the region configured to be severed includes a visual indicator that extends in a direction substantially perpendicular to an extension of the elongated member.

7. The implant of claim 1, wherein the fastening member comprises at least a first opening and a second opening that are substantially aligned with an extension of the elongated member, and wherein the region configured to be severed is located between the first opening and the second opening.

8. The implant of claim 7, wherein the first opening is configured to be located proximate to a first bone portion and the second opening is configured to be located proximate to a second bone portion to be fixed.

9. An implant for bone fixation, comprising:
an elongated member defining a width between a first lateral side of the elongated member and a second lateral side of the elongated member, the elongated member being configured to be wound around bone portions that are to be fixed;
an engagement member coupled to the elongated member and configured to engage a portion of the elongated member so as to secure the implant in a loop around the bone portions;
a fastening member arranged between and coupled to the elongated member and the engagement member, the fastening member comprising at least one opening for receiving a bone fastener and at least one visual indicator having a region of reduced mechanical strength located between a first axis collinear with the first lateral side and a second axis collinear with the second lateral side, the at least one visual indicator indicating a region of the fastening member to be severed in order to open the loop of the implant, the fastening member being coupled to at least one of the elongated member and the engagement member by injection molding,
wherein the positioning of the implant around the bone portions locates the at least one visual indicator about a junction of the bone portions such that severing the at least one visual indicator opens the loop of the implant adjacent the junction of the bone portions.

10. The implant of claim 9, wherein the fastening member comprises a first end and a second end opposite to the first end, wherein the elongated member is injection molded to the first end of the fastening member and/or the engagement member is injection molded to the second end of the fastening member.

11. The implant of claim 9, wherein the elongated member comprises a plurality of engagement features provided along an extension of the elongated member, wherein the engagement member is configured to be brought into selective engagement with one of the engagement features.

12. The implant of claim 9, further comprising a hook member coupled to the elongated member at an end thereof opposite to the engagement member.

13. The implant of claim 12, wherein the hook member is coupled to the elongated member by injection molding.

14. The implant of claim 9, wherein the at least one opening of the fastening member comprises a locking feature configured to lock the bone fastener to the fastening member.

15. The implant of claim 9, wherein the fastening member is made from metallic material and the elongated member is made from a polymeric material.

16. A system for bone fixation, comprising:
an implant comprising:
an elongated member defining a width between a first lateral side of the elongated member and a second lateral side of the elongated member, the elongated member being configured to be wound around bone portions that are to be fixed;
an engagement member coupled to the elongated member and configured to engage a portion of the elongated member so as to secure the implant in a loop around the bone portions; and
a fastening member arranged between and coupled to the elongated member and the engagement member, the fastening member comprising at least one opening for receiving a bone fastener and a region configured to be severed in order to open the loop of the implant, wherein the region configured to be severed is a region of reduced mechanical strength and is located between a first axis collinear with the first lateral side and a second axis collinear with the second lateral side, and wherein the fastening member is coupled to at least one of the elongated member and the engagement member by injection molding; and
at least one bone fastener configured to be inserted through the at least one opening of the fastening member of the implant into bone.

17. The system of claim 16, wherein the at least one opening of the fastening member comprises a first locking feature configured to lock the bone fastener to the fastening member and wherein the bone fastener comprises a second locking feature configured to engage the first locking feature.

* * * * *